(12) United States Patent
Bateman et al.

(10) Patent No.: US 6,410,915 B1
(45) Date of Patent: Jun. 25, 2002

(54) MULTI-INLET MASS SPECTROMETER FOR ANALYSIS OF LIQUID SAMPLES BY ELECTROSPRAY OR ATMOSPHERIC PRESSURE IONIZATION

(75) Inventors: Robert H. Bateman, Knutsford; John A. Hickson, London, both of (GB)

(73) Assignee: Micromass Limited (GB)

( * ) Notice: Subject to any disclaimer, the term of this patent is extended or adjusted under 35 U.S.C. 154(b) by 0 days.

(21) Appl. No.: 09/335,116

(22) Filed: Jun. 17, 1999

(30) Foreign Application Priority Data

Jun. 18, 1998 (GB) .............................. 9813225
Jul. 27, 1998 (GB) .............................. 9816342

(51) Int. Cl.$^7$ .............................. H01J 49/26
(52) U.S. Cl. .................. 250/288; 250/281; 250/283
(58) Field of Search .................. 250/281, 282, 250/288

(56) References Cited

U.S. PATENT DOCUMENTS

| | | | |
|---|---|---|---|
| 3,640,110 A | * 2/1972 | Inoue ............................ | 72/56 |
| 4,209,696 A | 6/1980 | Fite ............................. | 250/281 |
| 4,531,056 A | 7/1985 | Labowsky et al. ........... | 250/288 |
| 4,542,293 A | 9/1985 | Fenn et al. .................. | 250/288 |
| 4,730,111 A | 3/1988 | Vestal et al. ................ | 250/288 |
| 4,977,320 A | 12/1990 | Chowdhury et al. ........ | 250/288 |
| 5,170,053 A | * 12/1992 | Hail et al. ................... | 250/288 |
| 5,202,563 A | * 4/1993 | Cotter et al. ................ | 250/287 |
| 5,436,446 A | 7/1995 | Jarrell et al. ................ | 250/288 |
| 5,498,545 A | * 3/1996 | Vestal ......................... | 436/47 |
| 5,504,327 A | 4/1996 | Sproch et al. ............... | 250/288 |
| 6,069,355 A | * 5/2000 | Mordehai .................... | 250/281 |
| 6,066,848 A | 6/2000 | Kassel et al. | |
| 6,191,418 B1 | 2/2001 | Hindsgaul et al. | |

FOREIGN PATENT DOCUMENTS

| | | | |
|---|---|---|---|
| GB | 1 584 459 | 2/1981 | ............ H01J/49/26 |
| GB | 2 308 227 A | 6/1997 | ............ H01J/49/04 |
| JP | 10074480 | 3/1998 | |
| WO | WO 94/16101 | 7/1994 | ............ C12Q/1/68 |
| WO | WO 97/29508 | 8/1997 | ............ H01J/40/04 |
| WO | WO 98/11595 | 3/1998 | ............ H01J/49/10 |
| WO | WO 99/13492 | 3/1999 | ............ H01J/49/26 |

OTHER PUBLICATIONS

Fenn et al, "Electrospray ionization–principles and practice", 1990, Mass Spectrometry Reviews, pp. 37–70.

Smith et al, "Principles and practice of electrospray ionization—mass spectrometry for large polypeptides and proteins", 1991, Mass Spectrometry Reviews, pp. 10 and 359–451.

Kostiainen et al, Effect of Multiple Sprayers on Dynamic Range and Flow Rate Limitations in Electrospray and Ionspray Mass Spectrometry, 1994, Rapid Communications in Mass Spectrometry, vol. 8, pp. 548–558.

(List continued on next page.)

Primary Examiner—Kiet T. Nguyen
Assistant Examiner—David A Vanore
(74) Attorney, Agent, or Firm—Everett G. Diederiks, Jr.

(57) ABSTRACT

An electrospray and/or atmospheric pressure ionization mass spectrometer includes an evacuated chamber, a sampling region within which is maintained a pressure greater than in the evacuation chamber, a sampling orifice that communicates between the sampling region and the evacuation chamber, and a mass analyzer that receives charged particles along a first axis through the sampling orifice from the sampling region into the evacuated chamber. A plurality of charged-particle jet generators, each having an associated jet axis, are adapted to be alternatively, selectively aligned such that a respective jet axis intersects with the first axis associated with the mass analyzer. This alignment is performed through the use of a hollow member which functions to guide charged particles through the sampling orifice to the evacuated chamber and, subsequently, to the mass analyzer.

45 Claims, 6 Drawing Sheets

OTHER PUBLICATIONS

Hagiwara et al, "Improvement of Measurement Repeatability for High Performance Liquid Chromatography/Atmospheric Pressure Chemical Ionization–Mass Spectrometry by Sample Introducing Method Using Auto Switching Valve", 1995, J. Mass Spectrom. Soc. Jpn., vol. 44, No. 2, pp. 249–259.

Rashed et al, "Screening blood spots for inborn errors of metabolism by electrospray tandem mass spectrometry with a microplate batch process and a computer algorithm for automated flagging of abnormal profiles", 1997, Clinical Chemistry, pp. 1129–1141.

Horning et al, "Liquid Chromatograph–Mass Spectrometer –Computer Analytical Systems / A Continuous–Flow System Based on Atmospheric Pressure Ionization Mass Spectrometry", 1974, Journal of Chromatography, 99, pp. 13–21.

Andrien et al, "Electrospray and APCI Interface for Mass Spectrometry", 1995, Spectroscopy 10(2), pp. 42–44.

* cited by examiner

MULTI-INLET MASS SPECTROMETER FOR ANALYSIS OF LIQUID SAMPLES BY ELECTROSPRAY OR ATMOSPHERIC PRESSURE IONIZATION

BACKGROUND OF THE INVENTION

This invention relates to mass spectrometers wherein the process of ionizing a sample involves the generation of a jet of charged particles. More particularly, it relates to mass spectrometers for the analysis of liquid samples by electrospray or atmospheric pressure ionization, but is also applicable to certain other types.

Complex mixtures of high molecular weight and/or thermally labile biomolecules are now routinely analyzed by electrospray or atmospheric pressure ionization mass spectrometry, often following separation by liquid chromatography or capillary electrophoresis. Most conveniently, to carry out such analyses the eluent from the chromatographic apparatus is fed directly to the electrospray or atmospheric pressure ionization source of a mass spectrometer. Both these ionization techniques are capable of generating intact molecular ions of very high molecular weight samples, and especially in the case of electrospray ionization, these ions may carry a large number of charges. This brings their mass-to-charge ratio into the range where it can be measured by relatively inexpensive mass analyzers such as quadrupoles or ion traps.

Both electrospray and atmospheric pressure ionization sources used for the analysis of solutions (rather than gases) involve the generation of a jet of charged particles in a region of high ambient pressure (typically atmospheric) and means for passing at least some of the charged particles into a region of lower pressure where they are mass analyzed. The jet typically comprises an aerosol of droplets produced from the solution, and the droplets may be at least partially desolvated by collisions with inert gas molecules in the region of high pressure.

In the case of an electrospray ionization source the aerosol is formed by maintaining a potential difference of between 3 and 6 kV between the exit of a capillary tube containing the solution to be analyzed and a counter electrode disposed downstream of it. The droplets comprised in the aerosol are electrically charged and are at least partially desolvated by collisions with molecules of an inert gas (usually heated) which is caused to flow through the region where the aerosol is formed. The charged particles so produced then pass through a nozzle-skimmer pressure reduction stage into an evacuated region where they are mass analyzed. In the case of many biomolecules the ions produced by electrospray ionization carry a large number of charges so that their mass-to-charge ratios may lie in the mass range of a quadrupole mass analyzer of moderate cost which could not be used if the ions were singly charged. Prior electrospray ionization sources are disclosed in U.S. Pat. Nos. 4,531,056, 4,542,293, 4,209,696, 4,977,320 and 5,504,327, PCT Patent Applications 95/24259, 98/11595 and 97/29508 and UK Patent Application 2,308,227. The technique of electrospray ionization has been reviewed by Fenn et. al. in Mass Spectrom. Rev. 1990, vol 9 pp 37–70 and Smith et. al. in Mass Spectrom. Rev. 1991 vol 10 pp 359–451.

Historically, API sources were developed for the analysis of trace materials in gases (for example, the source described in UK Patent 1,584,459), but are now extensively used for the analysis of liquids. In such a source the jet of charged particles is generated by first producing an aerosol of droplets from the solution by means of a nebulizer in a region of high ambient pressure, then charging the droplets by a separate ionization process, for example a corona discharge maintained between electrodes in the vicinity of the aerosol. Charged droplets so produced may be desolvated as in the case of an electrospray source and the charged particles so produced. See, for example, Homing, Carroll et al, J Chromatog. 1974 vol 99 pp 13–21. Instead of a corona discharge, other forms of ionization can be employed, for example a $^{63}$Ni radioactive foil, and many different types of nebulizer may be used. More recent ion sources based on these early devices are known as atmospheric pressure chemical ionization sources (APCI) because ionization is essentially a chemical ionization process, that is, the reaction of sample molecules with primary ions generated in the discharge or other means of primary ionization. In fact, a separate ionization process is not always required and in some ion sources the nebulization step itself generates a charged particle jet as a result of ion evaporation from the droplets which become electrically charged during their formation from the bulk liquid.

A further variation of API sources is known as thermospray ionization, in which the liquid is nebulized by causing it to flow through a strongly heated capillary tube. (See for example U.S. Pat. No. 4,730,111). This nebulization method often produces sufficient ions for subsequent mass analysis without an additional ionization step but may be assisted by a variety of methods such as a glow discharge or electron impact ionization. on sources that provide combinations of the features described, for use either imultaneously or as alternative nebulization or ionization methods in the same source, are also known. For example, most electrospray ion sources in current production also provide APCI capabilities. See, for example, Andrien and Boyle, Spectroscopy 1995 vol. 2 pp. 42–44, PCT patent applications 95/24259 and 98/11595 and GB patent application 2,308,227.

Charged particle jet sources of the types described are very frequently used to analyze the eluent from a liquid chromatograph, and are now employed in this way on a routine basis. The ability of these sources to interface directly to liquid chromatography and to produce characteristic ions from very high mass thermally labile molecules has recently created a demand for automated systems capable of analyzing many samples in as short a time as possible, for example in medical screening programs (for example, see Rasheed, Bucknall et al, Clin. Chem. 1997 vol 43:7 pp 1129–1141) and for DNA and protein sequencing (for example, PCT patent application 94/16101). Applications of this type require very high throughput if they are to be cost effective, but prior types of charged-particle source are capable of accepting the eluent of a single chromatograph only. An automatic flow-switching valve arrangement for a liquid chromatograph attached to an API source is taught by Hagiwara et al. (J. Mass Spectrom. Sec. Japan, 1996 vol 44 (2) pp 249–259) but this is intended to reduce contamination of the ion source during repeated analysis carried out by one chromatograph.

An electrospray ion source having several capillaries operating simultaneously is reported by Kostiainen and Brums (Rapid Commun. in Mass Spectrometry, 1994 vol 8 pp 549–58) but this apparatus is intended to improve ionization efficiency from a single flow of analyte. Andrien, Whitehouse, et. al, in PCT patent application WO 99/13492 (published Mar. 18, 1999) describe a multiple inlet electrospray/API mass spectrometer in which at least two of the solutions introduced are simultaneously ionized. The mixture of ions generated from the two solutions is then introduced into a mass analyzer. However, such simultaneous introduction inevitably results in mass spectral data that represents a mixture of the two solutions and the method is therefore limited in its applicability.

SUMMARY O THE INVENTION

It is an object of the present invention, therefore, to provide a mass spectrometer comprising a charged-particle jet ionization source that is capable of receiving a plurality of fluid streams, each comprising a sample to be analyzed, without simultaneously introducing ions from more than one of the fluid streams into the mass analyzer of the spectrometer. It is another object of the invention to provide such a spectrometer that can produce mass spectral data from all of the streams quickly enough to allow the analysis of species in the streams that have been separated by high resolution liquid chromatography.

It is further object to provide methods of mass spectrometry using a charged-particle jet ionization source to analyze a plurality of fluid streams without simultaneously introducing ions from more than one of the streams into a mass analyzer. Another object of the invention is to provide such methods that are fast enough to allow the analysis of species in the fluid streams that have been separated by high resolution liquid chromatography. Further objects of the invention are to provide mass spectrometers comprising electro spray, thermo spray and/or APCI ion sources capable of analyzing more than one flow of fluid and methods of operating those mass spectrometers. It is yet another object to provide a liquid chromatograph mass spectrometer comprising a plurality of chromatographs which can be operated simultaneously and still another object to provide methods of operating it.

In accordance with these objectives the invention provides a mass spectrometer comprising an evacuated chamber, a sampling region where the pressure is greater than in said evacuated chamber, a sampling orifice communicating between said sampling region and said evacuated chamber, and a mass analyzer which receives at least some charged particles which pass along a first axis through said sampling orifice from said sampling region into said evacuated chamber, said spectrometer characterized by the further provision of:

a) a plurality of charged-particle jet generation means each of which is supplied with a fluid to be analyzed and generates a jet, aligned with a jet axis, of charged particles derived from said fluid, disposed so that each generation means has a different jet axis and so that all said jet axes intersect said first axis within said sampling region;

b) jet selecting means comprising a hollow member disposed so that the intersections of said jet axis and said first axis are within its interior, said hollow member having at least a first aperture alignable with said jet axis through which at least some charged particles comprised in a said charged-particle jet may enter the interior of said hollow member and travel to said first axis; and c) means for aligning said aperture in said hollow member with each said jet axis in turn, thereby allowing in turn at least some charged particles comprised in each said jet to enter the interior of said hollow member to pass through said sampling orifice into said evacuated chamber, and subsequently to enter said mass analyzer.

In preferred embodiments at least a second aperture is provided in the hollow member of said jet-selecting means through which a charged particle jet entering through the first aperture may exit from the interior after intersecting the first axis. In this way the charged-particle jet suffers minimal disturbance when it is selected.

In a further preferred embodiment the invention provides an electrospray ionization mass spectrometer in which at least one said charged-particle jet generation means comprises an aerosol generation means maintained at a high potential relative to counter electrode means disposed downstream of it. Said counter electrode means may conveniently comprise said hollow member which may be made of an electrically conductive material, and/or an additional counter electrode disposed in the path of the jet of charged particles which exits from said hollow member when the apertures in it are aligned with the jet axis of the aerosol generation means. Said aerosol generation means may comprise a capillary tube. Preferably, a nebulizing gas is supplied to the exit of the capillary tube by means of a tube coaxial with the capillary tube to assist with the formation of the aerosol, as in prior types of single-jet electrospray sources. A heated drying gas may also be supplied to the exit of the aerosol generation means in said sampling region to assist desolvation of the droplets produced in the aerosol.

In an alternative embodiment an atmospheric pressure ionization mass spectrometer is provided, in which each charged-particle generation means comprises aerosol generation means for generating droplets from said fluid and means for electrically charging the droplets so produced. Aerosol heating means may also be provided for desolvating the droplets produced by the aerosol generating means. Conveniently the means for electrically charging the droplets may comprise a discharge electrode disposed in said sampling region and maintained at a potential which results in the formation of a corona discharge. The aerosol generating means may comprise a tube for supplying a nebulizing gas, as in the case of the electrospray jet generation means described above.

It is not necessary for all of the charged particle jet generation means to be identical. It is within the scope of the invention to use, for example, two electrospray ionization generation means and two atmospheric pressure ionization generation means. Further, one or more of the charged-particle jet generation means may comprise a thermospray ionization device, wherein ionization of the sample is effected by strongly heating a capillary tube through which the sample solution is flowing.

It is also advantageous to use one of the charged particle jet generation means to introduce a calibration compound for the mass spectrometer. In this way the mass spectrometer calibration may be updated during each sampling cycle and the mass measurement accuracy of the mass spectrometer consequently improved.

In further preferred embodiments the charged-particle jet generation means are radially disposed so that the jets they produce are directed towards said first axis, the means for aligning said aperture may comprise motor means for rotating said hollow member to bring an aperture in line with each of the charged-particle jet generation means in turn. Conveniently, the jets may be arranged to be perpendicular to the first axis, but this is not essential. This radial disposition allows at least some of the charged particles produced by each generation means to pass through the sampling orifice and be analyzed by the mass analyzer. If, as is preferred, more than one aperture is provided, these are typically arranged as diametrically opposed pairs so that in any given position of the hollow member where one aperture is aligned with one of the charged-particle generation means the other aperture of the pair provides an exit aperture through which the charged-particle jet may escape from the hollow member with minimal disturbance. In a preferred embodiment, two apertures are provided disposed directly opposite to one another and the hollow member is rotated to align the apertures in it with a particular jet axis.

The charged-particle jet generation means may be disposed around an arc of less than 180° centered on said first axis. As the hollow member rotates, one aperture in it serves first to allow charged particles from each jet in turn to enter the hollow member while the other serves as a corresponding exit aperture. Further rotation of the hollow member then reverses the role of the two apertures so that the aperture previously serving as the exit aperture then becomes the entrance aperture during the next 180° of rotation of the hollow member. It will be appreciated that more apertures can be provided if desired, providing that the arc around which the charged-particle jet generators are arranged is less than the angle between adjacent apertures in the hollow member.

Further preferably movement of the hollow member is stopped for a predetermined time period when an aperture in it is aligned with each of the charged-particle jet generation means in turn. This allows charged particles to be sampled from each generation means in turn for the predetermined time period without interference from the charged particles produced by the other generation means. Relevant data from the mass spectrometer is then acquired only while a particular charged particle jet is being sampled. Means may be produced for associating the data being acquired with the generation means being sampled at that time, for example by detecting the position of the jet selection means and flagging the corresponding data accordingly.

Apparatus according to the invention may also comprise a plurality of chromatographs, each feeding its eluent to a different charged-particle jet generation means. Typically, liquid chromatographs will be used in conjunction with electrospray ionization, but gas chromatographs or capillary electrophoresis separation devices may also be employed. Using four such chromatographs and their corresponding generation means disposed at 45° to each other, a jet selection means comprising two apertures may sample each chromatograph eluent for 0.1 seconds and take 0.1 seconds to move between each of the generation means. Thus a complete mass spectrum may be generated for every chromatograph more frequently than once per second while four chromatographic analyses are being carried out.

Any convenient type of mass analyzer may be used in the invention, for example, magnetic sector, quadrupole, ion trap or time-of-flight analyzers, and tandem mass spectrometers such as triple-quadrupole mass spectrometers. Time-of-flight and ion-trap mass analyzers are especially appropriate because of their ability to substantially simultaneously detect ions of all mass-to-charge ratios. Consequently, an undistorted complete spectrum can be recorded in a shorter time while the jet selection means is sampling charged particles from any particular jet generation means than would be possible with a scanning mass analyzer. The data so acquired may then be processed in the time period when the jet selection means is moving between the generation means so that the analyzer is able to start acquisition as soon as the jet selection means is aligned with the next generation means. In this way it is possible to speed up the rate at which each of the jet generation means is sampled, thereby minimizing the loss of time-varying data from each of the generation means. However, tandem mass spectrometers, especially triple-quadrupole mass spectrometers, also benefit from the greater sample throughput that can be achieved using the present invention.

Viewed from another aspect the invention provides a method of mass spectrometry comprising mass analyzing charged particles which pass into an evacuated chamber through a sampling orifice along a first axis from a sampling region in which the pressure is greater than in the evacuated chamber, said method characterized by:

a) supplying a fluid to be analyzed to each of a plurality of charged-particle jet generator means to generate jets of charged particles derived from said fluid along a jet axis, each said charged-particle jet generation means having a different jet axis and each said jet axis intersecting said first axis within said sampling region; and b) selecting in turn each of at least some of the jets of charged-particles by aligning with them a first aperture in a hollow member within whose interior said jet axis and said first axis intersect so that charged particles comprised in the jet so selected may enter the interior of said hollow body and travel to said first axis and at least some of said charged-particles pass along said first axis through said sampling orifice into said evacuated chamber.

A preferred method further comprises allowing said selected jet to exit through a second aperture in said hollow member. In other preferred methods the jet of charged particles is produced by electrospray ionization, for example by generating an aerosol of droplets at a high potential relative to counter electrode means disposed downstream of the charged-particle jet generation means. Alternatively, or in addition, the jet of charged particles may be produced by atmospheric pressure ionization, for example by generating an aerosol and electrically charging the droplets so produced by means of a corona discharge.

Further preferred methods according to the invention comprise repeating the cycle of mass analyzing in turn each of at least some of said jets of charged particles and acquiring mass spectral data for each selected jet of charged particles during a plurality of said cycles. In preferred methods the step of mass analyzing the charged particles comprises measuring their mass-to-charge ratios using a time-of-flight or an ion trap mass analyzer, but tandem mass analyzers, such as a triple-quadrupole can also be used. Still further preferred methods comprise selecting a said jet of charged particles for a predetermined time by maintaining said hollow member in a fixed position and acquiring mass spectral data for said predetermined time, then aligning said hollow member to select the next of said jets of charged particles for which mass spectral data acquired. inhibiting the acquisition of data while said alignment is taking place.

Typically, the fluid supplied to each of the charged-particle jet generation means comprises the eluent from a chromatograph. Thus the invention provides a method of carrying out simultaneously the mass spectral analysis of the eluent from a plurality of chromatographs without the need for a plurality of mass spectrometers or switching the eluent flows directly.

BRIEF DESCRIPTION OF THE DRAWINGS

Preferred embodiments of the invention will now be described in greater detail by reference to the figures, in which.

DETAILED DESCRIPTION OF THE PREFERRED EMBODIMENTS

Figure 1:
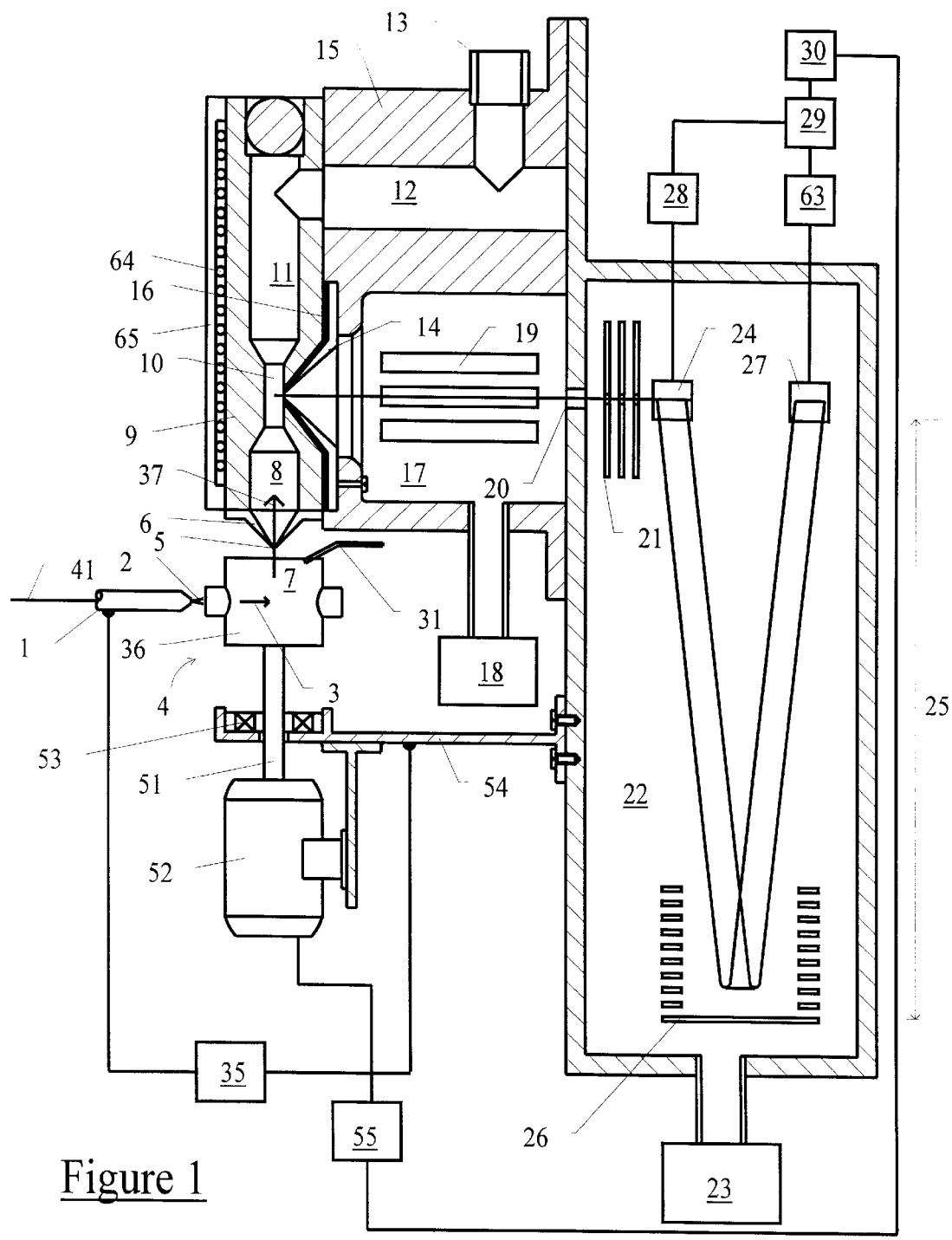
FIG. 1 is a sectional schematic drawing of a time-of-flight mass spectrometer according to the invention.

Referring first to FIG. 1, a mass spectrometer according to the invention comprises a plurality of charged-particle jet generation means (one of which is shown at 1) which generate a jet of charged particles 2 along a jet axis 3 (see also FIG. 2) and a jet selection means generally indicated by 4, described in more detail below. A sampling orifice 5 formed in the apex of a cone 6 provides communication between a sampling region 7 and an evacuated chamber 8 formed in a sampling body 9. The evacuated chamber 8 is evacuated through an extraction region 10, via the passageways 11 and 12 and the port 13 and is maintained at a pressure of between about 1 and 5 mmHg. A hollow conical member 14 is fitted in an adapter 15 (made from a filled PTFE such as PEEK) to which the sampling body 9 is attached. The hollow conical member 14 comprises an orifice in its apex through which charged particles may pass from the extraction chamber 10 into its interior. An insulating washer 16 prevents electrical contact between the hollow conical member 14 and the sampling body 9, allowing a potential difference to be maintained between the body 9 and the hollow conical member 14. The interior of the hollow conical member 14 is in communication with a second evacuated chamber 17 which is evacuated by a vacuum pump 18 and contains a hexapole ion guiding device 19. Chamber 17 is maintained at about $10^{-2}$–$10^{-3}$ mm Hg by the pump 18. Ions which pass from the extraction region 10 through the hollow conical member 14 are then transmitted through the guiding device 19 through an orifice 20 into a third evacuated chamber 22 maintained at a pressure of less than $10^{-5}$ mm Hg by a vacuum pump 23. Conveniently, the guiding device 19 may comprise an RF-only hexapole ion guide which results in optimum ion transmission without significant mass discrimination, but other types of ion guides can also be used. A conventional orthogonal-acceleration time-of-flight mass analyzer comprising an ion pusher 24, a drift region 25, an ion reflector 26 and an ion detector 27 is contained within the third evacuated region 22. Ions entering the third evacuated chamber 22 through the orifice 20 are focussed into the ion pusher 24 by an electrostatic lens 21. Ion ejection pulses are supplied to the ion pusher 24 by a pulse generator 28 controlled by an analyzer controller 29 which also receives a signal from the ion detector 27 via the detector signal processor 63. A digital computer 30 is provided for processing the data generated by the time-of-flight mass analyzer and controlling the complete spectrometer. Operation of the time-of-flight mass analyzer is conventional.

A heater 64 enclosed by a cover 65 is attached to the sampling body 9 and is used to maintain the sampling body 9 at any desired temperature. For the analysis of thermally labile samples such as proteins a temperature of about 70° C is suitable, but higher temperatures, up to approximately 150° C, may be beneficial for more stable samples.

When the jet selection means 4 is positioned so that apertures in it are aligned with one of the jet axes 3, charged particles produced by one of the selected charged-particle jet generation means 1 pass through the sampling region 7. In the embodiment shown in FIG. 1 the jet generation means 1 comprises an electrospray probe (shown in greater detail in FIG. 3), the capillary of which is maintained at a high potential relative to a counter electrode which comprises the hollow member 36 (part of the jet selection means 4) by means of a power supply 35, thereby generating an electrosprayed jet of charged particles 2 in the sampling region 7. At least some of these charged particles enter the first evacuated chamber 8 through the orifice 5 along a first axis 37, then pass into the extraction region 10 and are subsequently mass analyzed, as explained.

Figure 2:
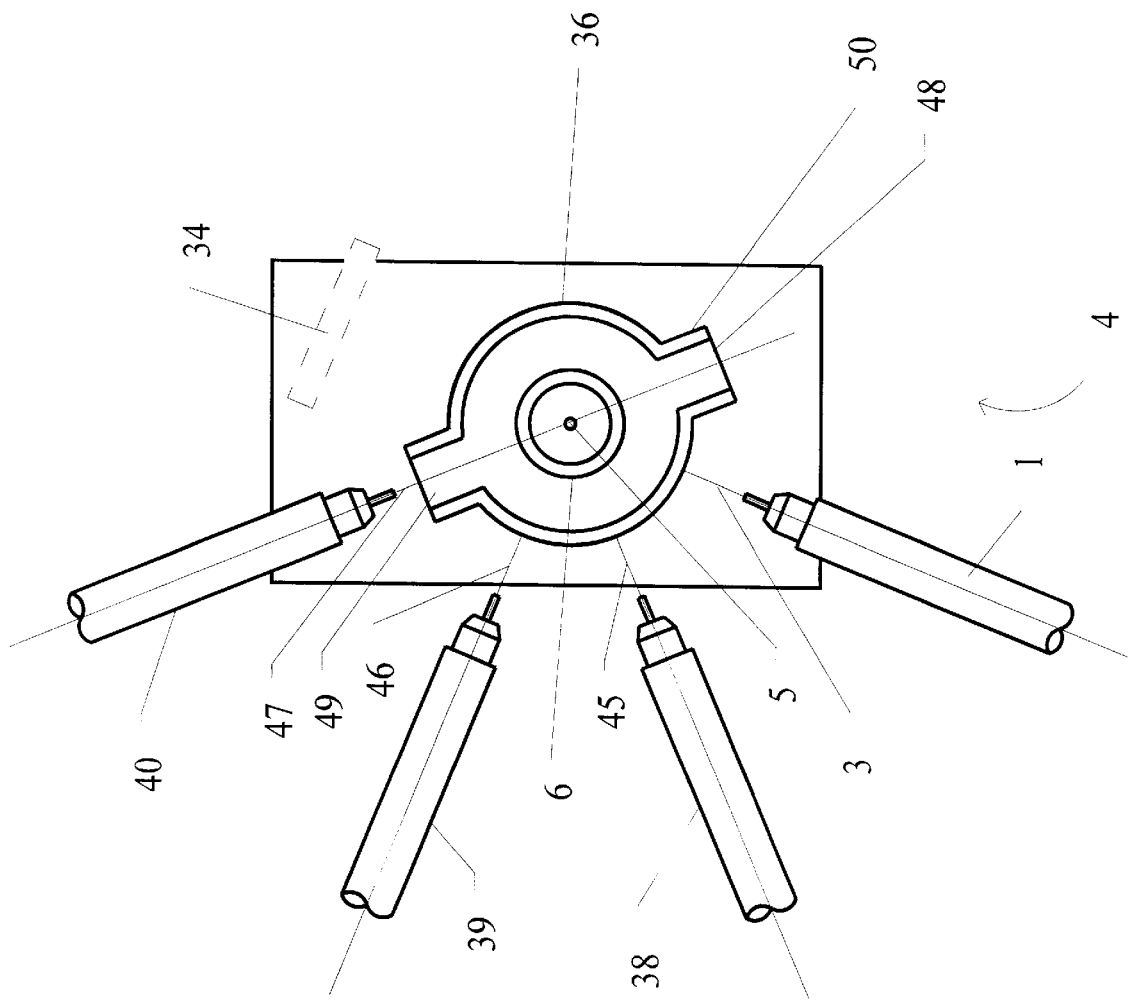
FIG. 2 is a drawing of a jet selection means suitable for use in the spectrometers illustrated in FIGS. 1 and 6.

Referring next to FIG. 2, which shows the jet selection means 4 in greater detail, four electrospray jet generation means 1, 38–40 are disposed at 45° to one another so that their tips are arranged on an arc centered on the axis 37 (FIG. 1). The jet generation means are disposed in a plane 41 (FIG. 1), perpendicular to the first axis 37. In this embodiment, the hollow body member 36 (see below) serves as a counter electrode for each of the electrospray jet generation means 1, 38–40, and no additional counter electrodes are provided. However, in other embodiments counter electrodes may be provided, for example in the position indicated by the dotted box 34 for the jet generation means 1. Each jet generation means is continuously supplied with a fluid to be analyzed and generates a continuous electrospray along jet axis 3, 45–47 respectively. As can be seen, each jet generation means 1 has a different jet axis 3, and all the jet axes intersect the first axis 37 in the sampling region 7.

An electrically-conductive hollow member 36 of substantially cylindrical form comprises two apertures 48, 49 through which each jet axis 3, 45–47 may pass when the member 36 is aligned with them, permitting charged particles from the selected electrospray jet generation means to pass into the sampling region 7. The sampling region 7 will of course be at a pressure above that of the evacuated chamber 8. It may be at atmospheric pressure, or, especially in the case of electrospray sources, somewhat above or below atmospheric pressure. Baffle tubes 50 are provided on the hollow member 36 to ensure that material from the unselected jet generation means does not enter the sampling region 7.

The hollow member 36 is mounted on the shaft 51 of a stepping motor 52 and supported by a bearing 53 mounted on a bracket 54, as shown in FIG. 1. Motor 52 is controlled by a motor controller 55 which in turn is controlled by the computer 30.

In use, once the four electrospray jets are established, the computer 30 causes the stepping motor 52 to rotate the hollow member 36 until its apertures are aligned with the jet axis 3 associated with the charged-particle jet generation means 1 so that the jet 2 of charged particles it produces enters the sampling region 7. At least some of the charged particles in the jet 2 then pass through the orifice 5 and are mass analyzed. The computer 30 is programmed to hold the hollow member 36 in this position for a predetermined time (typically 0.1 seconds) while mass spectral data is stored, after which it advances the hollow member so that its apertures are aligned with the jet axis 45 associated with the charged-particle jet generation means 38, and again holds the hollow member in position while mass spectral data is acquired. During the time while the hollow member is actually moving, computer 30 processes the data acquired from the detector signal processor 63 so that the mass analyzer is ready to acquire data as soon as the hollow member is aligned with the next jet axis.

The rotation and pause cycle of the hollow member continues until each of the charged-particle jet generation means has been sampled, and the whole process is repeated, storing the mass spectral data in synchronism with the rotation of the hollow member. In this way, mass spectral data for each of the separate fluids fed to the charged-particle jet generation means may be acquired over an extended time period.

Figure 3:
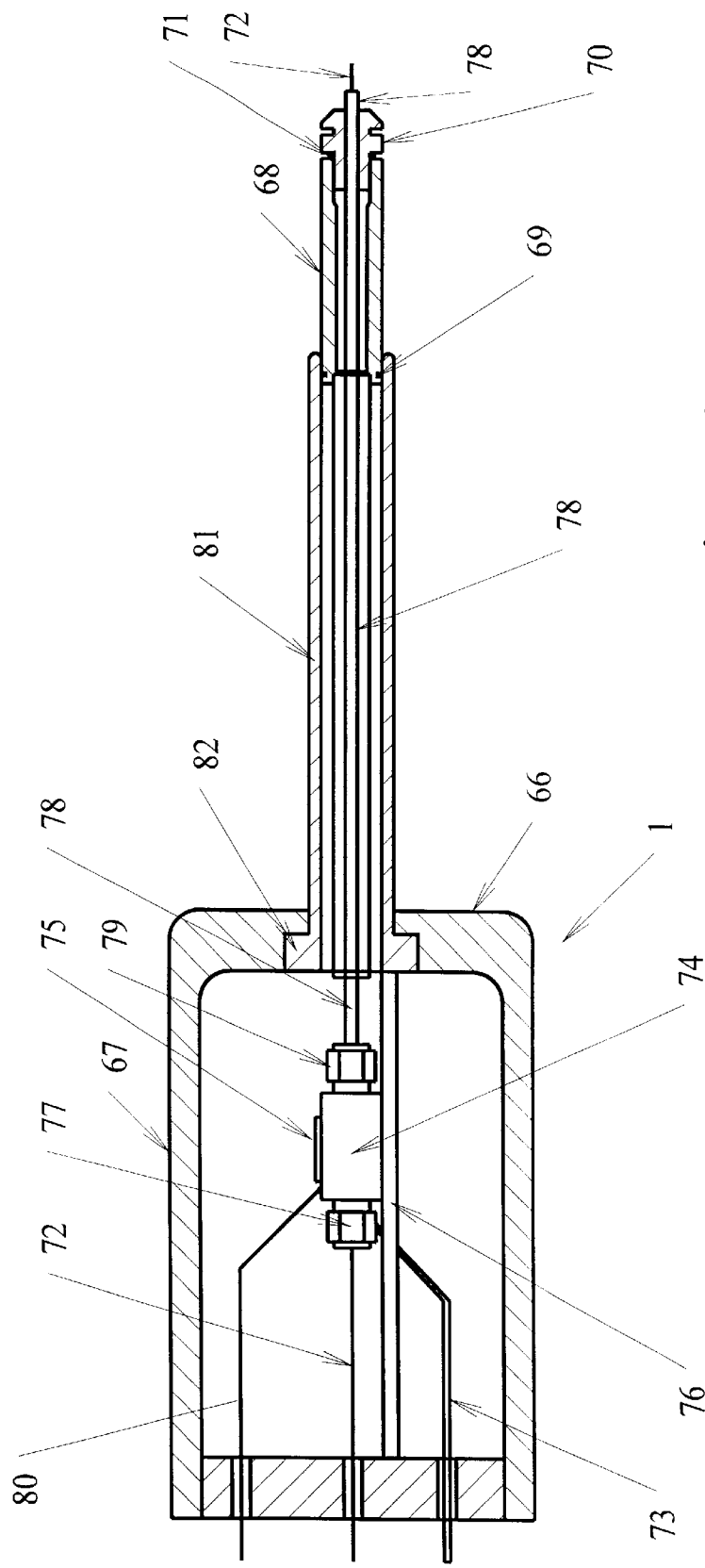
FIG. 3 is a drawing of a charged-particle jet generation means suitable for use in the spectrometers illustrated in FIGS. 1 and 6.

An electrospray jet-generation means 1 suitable for use with the invention is shown in FIG. 3. It comprises a hollow probe shaft 81 made of a rigid insulating material comprising a flange 82 which is located in a recess in the end wall 66 of a cylindrical housing 67. A stainless steel shaft extension 68 is sealed into the end of the shaft 64 by means of a 'O' ring 69, and a hollow stainless steel tip 70 is sealed into the end of the extension 68 by means of a second 'O' ring 71. A narrow bore small diameter capillary tube 72, also of stainless steel, runs the entire length of the probe assembly and is connected at the end remote from the tip 70 to a source of the solution to be analyzed, for example a liquid chromatographic column.

A supply of nebulizing gas (e.g., nitrogen) is fed via the pipe 73 to a 'T' connector 74 which is attached by a clamp 75 to a support plate 76 fixed in the housing 67. The capillary tube 72 passes straight through the remaining two unions on the 'T' connector 74 and is sealed in the union 77. A length of larger bore tube 78 through which the capillary tube 72 passes without a break, is sealed in the union 79 on the 'T' connector 74 and extends through the hollow interiors of the probe shaft 81, the shaft extension 68, and the probe tip 70. The capillary tube 72 protrudes about 0.5 mm from the end of the tube 78 so that the nebulizing gas emerges from the tube 78 and assists the electrostatic nebulization of the solution emerging from capillary tube 72.

In order to cause the electrospray ionization, the electrospray power supply 35 (FIG. 1) is connected to the 'T' connector 74 by the lead 80 so that the connector and the tubes 78 and 72 are maintained at the electrospray potential. A drying gas, typically heated nitrogen, is introduced into the sampling region 7 through a pipe 31 in order to assist the desolvation of the aerosol produced by the electrospray jet generation means, as in conventional electrospray ionization sources.

Figure 4:
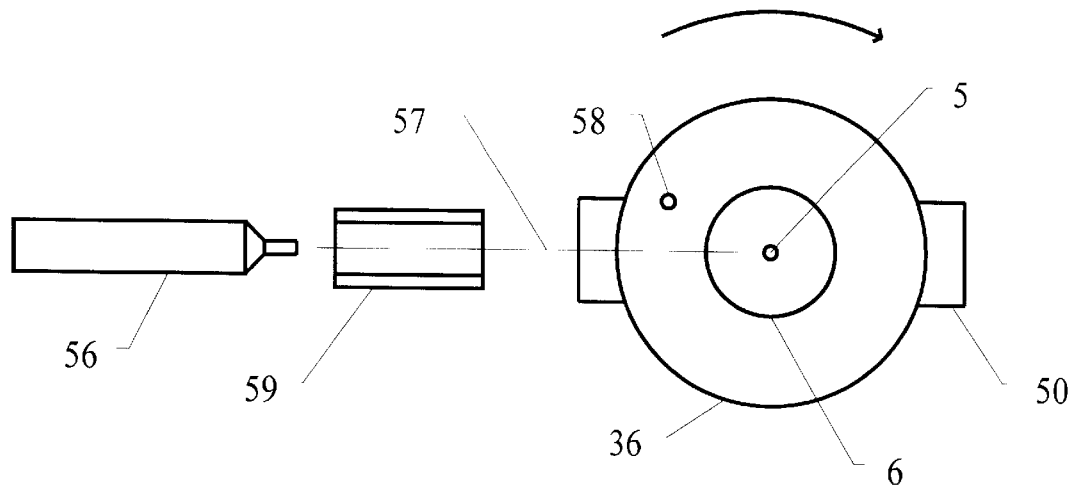
FIG. 4 is a drawing showing an atmospheric pressure ionization jet generation means suitable for use in the spectrometers illustrated in FIGS. 1 and 6.

As explained, the charged-particle jet generation means 1, 38–40 may comprise an atmospheric pressure ionization jet generation means instead of an electrospray ionization jet generation means. FIG. 4 shows such a generation means. A coaxial flow nebulizer 56 (similar to the arrangement shown in FIG. 3) and an aerosol heating means comprising a strongly heated tube 59 produce an aerosol in the sampling region 7 whenever the apertures in the jet selection means 4 are aligned with it. A corona discharge is produced in the sampling region 7 (when the nebulizer 56 is selected) by means of a high potential applied to a discharge electrode 58 (also shown in FIG. 5). Charged particles produced in the discharge travel along the jet axis 57 to the interior of the hollow member 36 as does the electrospray shown in FIGS. 1 and 2. Jet generation means according to FIG. 4 may replace any or all of the jet generation means 1, 38–40 of FIG. 2.

Figure 5:
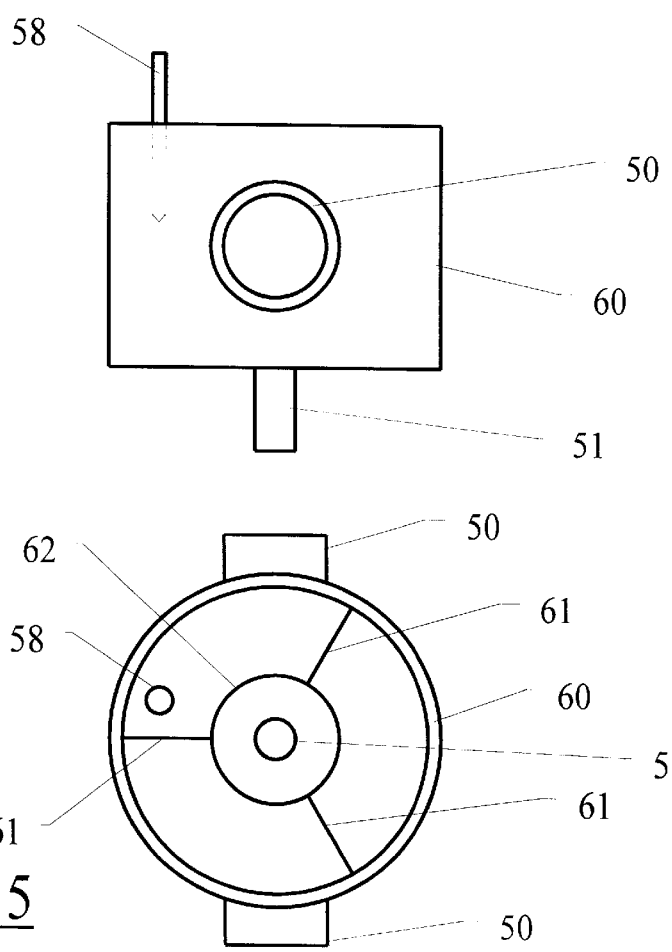
FIG. 5 is a drawing showing more details of the jet selection means of FIG. 2.

FIG. 5 shows in more detail the hollow member 36. It comprises an electrically conductive open-ended cylinder 60 to which two diametrically opposed baffle tubes 50 are attached as shown. The cylinder 60 is supported on the shaft 51 of the stepping motor 52 by means of a spider comprising three radial arms 61 attached to a central bush 62 fitted to the shaft 51. Such an open-ended construction ensures that the gas present in its interior does not differ greatly in composition from that in the remainder of the sampling region 7 in which the hollow member is disposed, and minimizes "crosstalk" between the various jet generation means.

Figure 7:
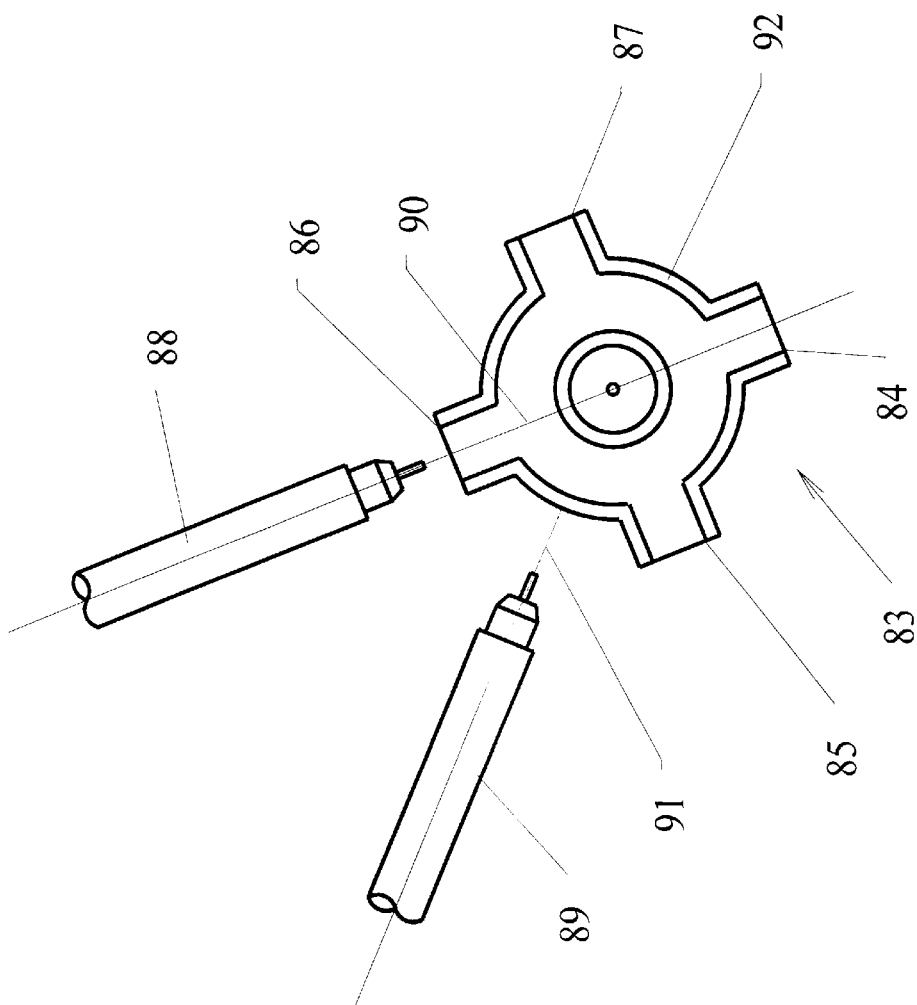
FIG. 7 is a drawing of an alternative jet selection means suitable for use in the spectrometers of FIGS. 1 and 6.

Referring next to FIG. 7, another preferred embodiment of the invention comprises the jet selection means 83. Two jet generation means 88 and 89 are disposed at 45° to each other so that their tips are arranged in an arc centered on the axis 37 in a similar manner to the arrangement illustrated in FIG. 2. The jet generation means 88, 89 have jet axes 90, 91 respectively. An electrically conductive hollow member 92 comprises four apertures 84–87, arranged in diametrically opposed pairs 86, 84 and 85, 87. As can be seen from the figure, as the hollow member 92 is rotated, first the pair of apertures 86, 84 are aligned with jet axis 90, allowing the jet produced by the generation means 88 to pass through the sampling region inside the hollow member 92. Further rotation of the hollow member 92 aligns the pair of apertures 85, 87 with the jet axis 91 and allows the jet formed by jet generation means 89 to pass into the sampling region. Continued rotation aligns apertures 85, 87 with jet axis 90, then apertures 84, 86 with jet axis 91, etc. This embodiment is particularly suitable when only a small number of jet generation means are employed. Its use may increase the efficiency of the spectrometer because apertures through which a jet may pass into the sampling region occupy a greater portion of the surface of the hollow member 92. However, it requires a closer spacing of the jet generation means than does the embodiment shown in FIG. 2, which is generally preferred if four or more jet generation means are provided.

Figure 6:
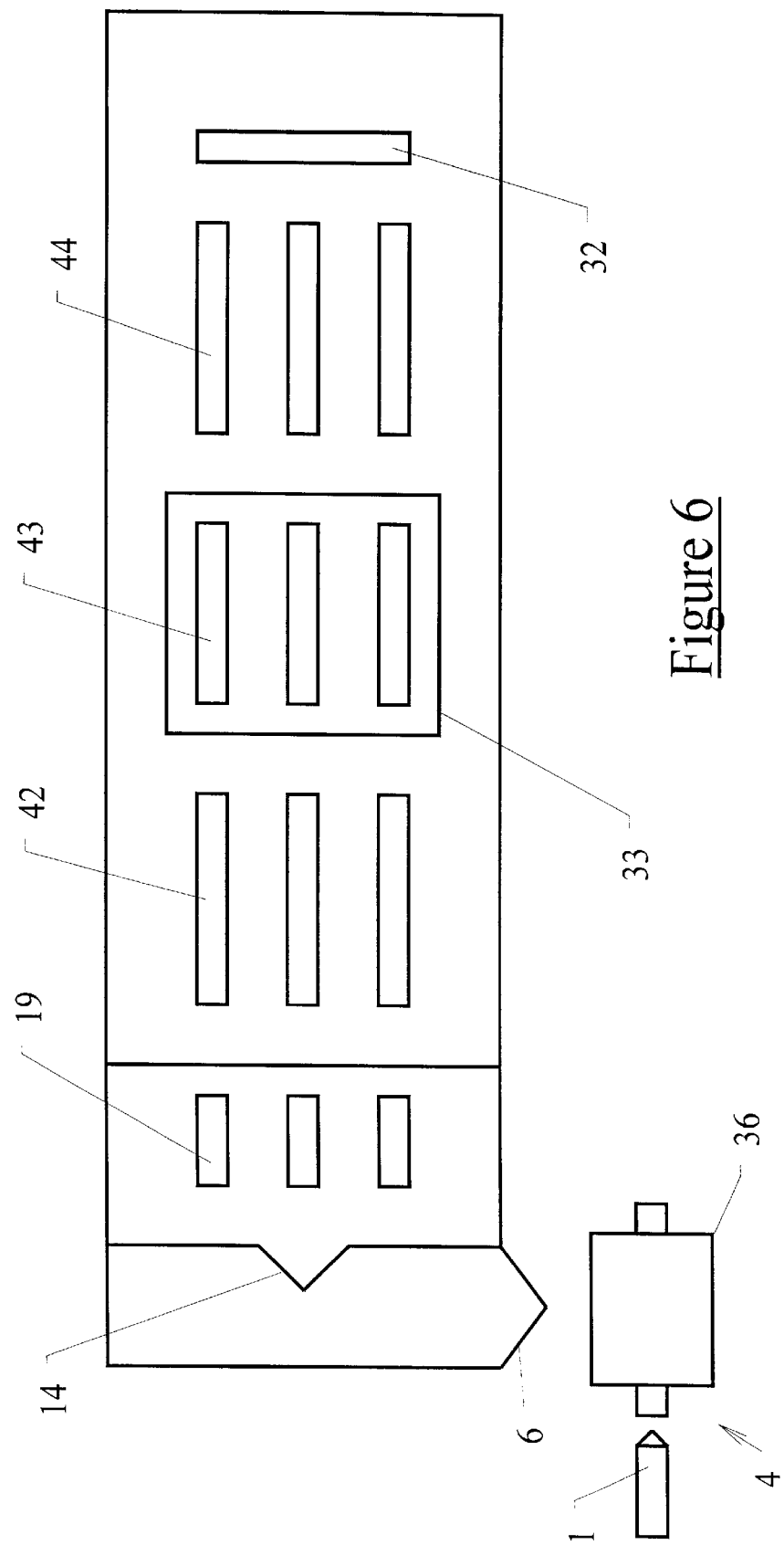
FIG. 6 is an outline drawing of a triple quadrupole tandem mass spectrometer according to the invention.

FIG. 6 is a highly simplified outline drawing of a tandem mass spectrometer (a triple quadrupole) according to the invention. The main components of the ion introduction system, comprising a plurality of charged-particle jet generation means 1, a jet selection means 4, a sampling cone 6 and an ion guiding means 19, etc, are shown in greater detail in FIG. 1. In place of the orthogonal-acceleration time-of-flight mass analyzer illustrated in FIG. 1, a triple quadrupole analyzer is provided. This comprises a first stage mass-selecting quadrupole 42, a collision cell comprising an RF only hexapole 43 enclosed in a substantially gas tight enclosure 33, a second-stage mass analyzing quadrupole 44 and an ion detector 32. The collision cell is used for fragmenting ions passed to it from the first quadrupole 42. Such triple quadrupole mass analyzers are well known and need not be described in detail.

In use, samples present in solutions fed to the charged-particle jet generation means 1 are ionized as previously described. Ions formed from the jet selected at any particular instant by the selection means 4 pass through the sampling cone 6, hollow conical member 14 into the triple quadrupole analyzer. Typically, ions having predetermined mass-to-charge ratios are selected by the first quadrupole 42 and enter the collision cell 42, 33. Here they are fragmented by collisions with inert gas molecules, and the fragment ions so produced are mass analyzed by the second quadrupole 44. However, any of the established methods of using a triple quadrupole analyzer may be used. The operation of the jet selection means 4 and the link between the mass spectral data generated and the selected jet may be performed as previously described.

What is claimed is:

1. A mass spectrometer comprising an evacuated chamber, a sampling region where in use the pressure is greater than in said evacuated chamber, a sampling orifice communicating between said sampling region and said evacuated chamber, and a mass analyzer which receives at least some charged particles which pass along a first axis through said sampling orifice from said sampling region into said evacuated chamber, said spectrometer being characterized by:

(a) a plurality of charged-particle jet generation means each of which is supplied with a fluid to be analyzed and generates a jet, aligned with a jet axis, of charged particles derived from said fluid, disposed so that each generation means has a different jet axis and so that all said jet axes intersect said first axis within said sampling region;

(b) jet selecting means comprising a hollow member disposed so that the intersections of said jet axis and said first axis are within its interior, said hollow member having at least a first aperture alignable with said jet axis through which at least some charged particles comprised in a said charged-particle jet may enter the interior of said hollow member and travel to said first axis; and (c) means for aligning said aperture in said hollow member with each said jet axis in turn, thereby allowing in turn at least some charged particles comprised in each said jet to enter the interior of said hollow member to pass through said sampling orifice to said evacuated chamber, and subsequently to enter said mass analyzer.

2. The mass spectrometer of claim 1, wherein at least a second aperture is provided in the hollow member of said jet selecting means through which a charged-particle jet entering through the first aperture may exit from the interior after intersecting the first axis.

3. The mass spectrometer of claim 1, wherein at least one of the charged-particle jet generation means comprises an aerosol generation means maintained at a high potential relative to counter electrode means disposed downstream of it in order to generate ions by electrospray ionization.

4. The mass spectrometer of claim 3, wherein said counter electrode means is the hollow member and the hollow member is made of an electrically conductive material.

5. The mass spectrometer of claim 3, wherein the aerosol generation means comprises a capillary tube and means for supplying a nebulizing gas to the exit of the aerosol generation means to assist the formation of the aerosol.

6. The mass spectrometer of claim 1, wherein at least one of the charged-particle generation means comprises aerosol generation means for generating droplets from said fluid and means for electrically charging the droplets so produced, in order to generate ions by atmospheric pressure ionization (API).

7. The mass spectrometer of claim 6, further comprising an aerosol heating means for desolvating the droplets produced by the aerosol generating means.

8. The mass spectrometer of claim 6, wherein the means for electrically charging the droplets comprises a discharge electrode disposed in said sampling region and maintained at a potential which results in the formation of a corona discharge.

9. The mass spectrometer of claim 1, wherein a heated drying gas is supplied to the exit of the aerosol generation means in said sampling region to assist desolvation of droplets in said aerosol.

10. The mass spectrometer of claim 6, wherein a heated drying gas is supplied to the exit of the aerosol generation means in said sampling region to assist desolvation of droplets in said aerosol.

11. The mass spectrometer of claim 1, wherein the charged-particle jet generation means are radially disposed so that the jets they produce are directed towards said first axis, the means for aligning said aperture comprising motor means for rotating said hollow member to bring an aperture in line with each of the charged-particle jet generation means in turn.

12. The mass spectrometer of claim 11, wherein the jet selecting means has a plurality of apertures arranged as diametrically opposed pairs.

13. The mass spectrometer of claim 11, wherein the charged-particle jet generation means are disposed around an arc of less than 180° centered on said first axis.

14. The mass spectrometer of claim 11, further comprising means for stopping movement of the hollow member for a predetermined time period when an aperture in it is aligned with each of the charged-particle jet generation means in turn.

15. The mass spectrometer of claim 11, further comprising means for associating the mass spectral data being acquired at a given time with the generation means being sampled at that time.

16. The mass spectrometer of claim 1, wherein the jet selecting means has a plurality of apertures arranged as diametrically opposed pairs.

17. The mass spectrometer of claim 1, wherein the charged-particle jet generation means are disposed around an arc of less than 180° centered on said first axis.

18. The mass spectrometer of claim 1, further comprising means for stopping movement of the hollow member for a predetermined time period when an aperture in it is aligned with each of the charged-particle jet generation means in turn.

19. The mass spectrometer of claim 1, further comprising means for associating the mass spectral data being acquired at a given time with the generation means being sampled at that time.

20. The mass spectrometer of claim 1, further comprising one or more liquid chromatographs, each of which feeds at least some of its eluent to a different one of said plurality of charged-particle jet generation means.

21. The mass spectrometer of claim 11, further comprising one or more liquid chromatographs, each of which feeds at least some of its eluent to a different one of said plurality of charged-particle jet generation means.

22. The mass spectrometer of claim 1, further comprising one or more capillary electrophoresis separation devices, each of which feeds at least some of its eluent to a different one of said plurality of charged-particle jet generation means.

23. The mass spectrometer of claim 11, further comprising one or more capillary electrophoresis separation devices, each of which feeds at least some of its eluent to a different one of said plurality of charged-particle jet generation means.

24. The mass spectrometer of claim 1, further comprising means for introducing a calibration compound into at least one of said charged-particle jet generation means.

25. The mass spectrometer of claim 11, further comprising means for introducing a calibration compound into at least one of said charged-particle jet generation means.

26. The mass spectrometer of claim 1, wherein the mass analyzer comprises a time-of-flight analyzer.

27. The mass spectrometer of claim 11, wherein the mass analyzer comprises a time-of-flight analyzer.

28. The mass spectrometer of claim 1, wherein the mass analyzer comprises a tandem mass spectrometer.

29. The mass spectrometer of claim 11, wherein the mass analyzer comprises a tandem mass spectrometer.

30. The mass spectrometer of claim 1, wherein said mass analyzer comprises a triple quadrupole.

31. The mass spectrometer of claim 11, wherein said mass analyzer comprises a triple quadrupole.

32. A method of mass spectrometry comprising mass analyzing charged particles which pass into an evacuated chamber through a sampling orifice along a first axis from a sampling region in which the pressure is greater than in the evacuated chamber, said method being characterized by:

(a) supplying a fluid to be analyzed to each of a plurality of charged-particle jet generation means to generate jets of charged particles derived from said fluid along a jet axis, each said charged-particle jet generation means having a different jet axis and each said jet axis intersecting said first axis within said sampling region; and (b) selecting in turn each of at least some of the jets of charged-particles by aligning with them a first aperture in a hollow member within the interior of which said jet axis and said first axis intersect so that charged particles comprised in the jet so selected may enter the interior of said hollow member and travel to said first axis and at least some of said charged-particles pass along said first axis through said sampling orifice into said evacuated chamber to be mass analyzed.

33. The method of claim 32, further comprising allowing said selected jet to exit through a second aperture in said hollow member.

34. The method of claim 32, wherein at least one of the jets of charged particles is produced by electrospray ionization.

35. The method of claim 32, wherein at least one of the jets of charged particles is produced by atmospheric pressure ionization.

36. The method of claim 32, wherein the selection of said jets of charged particles is repeated to repetitively acquire mass spectral data for each selected jet of charged particles.

37. The method of claim 32, wherein the mass analyzing comprises measuring the mass-to-charge ratio of at least some of the charged particles using a time-of-flight analyzer.

38. The method claim 32, wherein the mass analyzing comprises fragmenting at least some of the ions entering said mass analyzer in a collision cell comprised in a tandem mass spectrometer.

39. The method of claim 32, wherein the selecting comprises selecting a jet of charged particles for a predetermined time by maintaining said hollow member in a fixed position and acquiring mass spectral data for said predetermined time, and aligning said hollow member to select the next of said jets of charged particles for which mass spectral data is acquired, inhibiting the acquisition of data while said alignment is taking place.

40. The method claim 32, wherein the fluid supplied to at least one of the charged-particle jet generation means comprises the eluent from a liquid chromatograph.

41. The method claim 39, wherein the fluid supplied to at least one of the charged-particle jet generation means comprises the eluent from a liquid chromatograph.

42. The method of claim 32, wherein the fluid supplied to at least one of the charged-particle jet generation means comprises the eluent from a capillary electrophoresis separation device.

43. The method of claim 39, wherein the fluid supplied to at least one of the charged-particle jet generation means comprises the eluent from a capillary electrophoresis separation device.

44. The method of claim 32, wherein a calibration compound is supplied to one of said charged-particle jet generation means.

45. The method of claim 39, wherein a calibration compound is supplied to one of said charged-particle jet generation means.

* * * * *